(12) United States Patent
Wanders

(10) Patent No.: US 10,335,267 B2
(45) Date of Patent: Jul. 2, 2019

(54) INTRAOCULAR LENS HAVING PARTLY OVERLAPPING ADDITIONAL OPTICAL ACTIVE SECTORS ON OPPOSITE SIDES

(71) Applicant: OCULENTIS HOLDING B.V., Eerbeek (NL)

(72) Inventor: Bernardus Franciscus Maria Wanders, Angerlo (NL)

(73) Assignee: OCULENTIS HOLDING B.V., Eerbeek (NL)

( * ) Notice: Subject to any disclaimer, the term of this patent is extended or adjusted under 35 U.S.C. 154(b) by 139 days.

(21) Appl. No.: 15/021,598

(22) PCT Filed: Sep. 12, 2014

(86) PCT No.: PCT/NL2014/050626
§ 371 (c)(1),
(2) Date: Mar. 11, 2016

(87) PCT Pub. No.: WO2015/037994
PCT Pub. Date: Mar. 19, 2015

(65) Prior Publication Data
US 2016/0220349 A1 Aug. 4, 2016

(30) Foreign Application Priority Data
Sep. 12, 2013 (NL) ...................................... 2011433

(51) Int. Cl.
*A61F 2/16* (2006.01)
*G02B 27/00* (2006.01)

(52) U.S. Cl.
CPC .......... *A61F 2/1618* (2013.01); *A61F 2/1613* (2013.01); *A61F 2/1616* (2013.01); *A61F 2/1637* (2013.01); *G02B 27/0075* (2013.01)

(58) Field of Classification Search
CPC .... A61F 2/1613; A61F 2/1616; A61F 2/1618; A61F 2/1637; A61F 2/164; A61F 2/1643; A61F 2/1645
See application file for complete search history.

(56) References Cited

U.S. PATENT DOCUMENTS 6,719,792 B2    4/2004  Baikoff
8,240,847 B2    8/2012  Holden et al.
(Continued)

FOREIGN PATENT DOCUMENTS

CN          1346250 A       4/2002
CN        101467092 B       1/2011
(Continued)

OTHER PUBLICATIONS

International Search Report, dated Jan. 12, 2015, from corresponding PCT application.
(Continued)

*Primary Examiner* — William H Matthews
(74) *Attorney, Agent, or Firm* — Young & Thompson

(57) ABSTRACT

An intraocular lens includes an optic having first and second sides. The optic has a first main lens surface at the first side, a second main lens surface at the second side, the first main lens surface providing a first main lens surface optical power, the second main lens surface providing a second main lens surface optical power, the first and second main lens surfaces providing a main lens having a main lens optical power and main optical axis defining radial, tangential and axial directions. The optic has: a first additional optical active part at the first side, providing a positive relative optical power with respect to the first main lens surface optical power; and a second additional optical active part at the second side, partly overlapping the first additional optical active part, providing a relative optical power and/or (Continued)

optical aberration with respect to the second main lens surface.

16 Claims, 4 Drawing Sheets

(56) References Cited

U.S. PATENT DOCUMENTS

| | | |
|---|---|---|
| 2005/0128432 A1 | 6/2005 | Altmann |
| 2010/0100177 A1 | 4/2010 | Zhao |
| 2012/0029631 A1 | 2/2012 | Wanders et al. |

FOREIGN PATENT DOCUMENTS

| | | |
|---|---|---|
| WO | 2006/056847 A1 | 6/2006 |
| WO | 2012/118371 A1 | 9/2012 |
| WO | 2013/080053 A1 | 6/2013 |

OTHER PUBLICATIONS

Chinese Search Report, dated Feb. 7, 2017, from corresponding Chinese application, includes English translation.

INTRAOCULAR LENS HAVING PARTLY OVERLAPPING ADDITIONAL OPTICAL ACTIVE SECTORS ON OPPOSITE SIDES

FIELD OF THE INVENTION

The presents invention relates to an intraocular lens (IOL) comprising an optic. The optic has first and second sides and comprises a first main lens surface at the first side and a second main lens surface at the second side, the first main lens surface providing a first main lens surface optical power and the second main lens surface providing a second main lens surface optical power, the first and second main lens surfaces providing a main lens having a main lens optical power and a main optical axis defining radial, tangential and axial directions. The optic further comprises a first additional optical active part at the first side, the first additional optical active part providing a positive relative optical power with respect to the first main lens surface optical power

BACKGROUND OF THE INVENTION

Such intraocular lenses are known. The first and second main lens surface constitute a main lens together with the material of the optic. The main lens is generally optimized for distance vision of the person having the IOL inserted in the eye and will correct for any optical errors of the eye to provide a project a good quality image of a distant object on the retina. The first additional power part generally is laid out to provide near or distance vision. It may be embodied as a sector in between the main optical axis and the circumference of the optic, which may take about half of the surface area of the optic at the first side, although other embodiments may be envisaged as well.

However, when someone is reading, especially at low light conditions, his or her pupils will become narrower. The effect of the first additional optical active part (reading part) will therefore become less effective for a person having an IOL inserted in the eye. This effect even becomes worse for persons having narrow pupils anyway. In such circumstances and especially for persons having narrow pupils the effect of the first additional power (reading) part may effectively be absent or only be very weakly present. Only distance vision remains available, which is a very unfavorable situation.

SUMMARY OF THE INVENTION

It is an object of the invention to provide an IOL that provides improved reading capabilities at narrow pupil sizes.

It is another or alternative object of the invention to provide an IOL providing improved reading ability at low light conditions.

It is another or alternative object of the invention to provide an IOL providing improved reading ability, which can be effectively and rather straightforwardly be produced.

It is yet another or alternative object of the invention to provide such IOL that does not effectively influence the distance vision capability.

At least one of the above objects is achieved by an intraocular lens comprising an optic, the optic having first and second sides and comprising:

a first main lens surface at the first side and a second main lens surface at the second side, the first main lens surface providing a first main lens surface optical power and the second main lens surface providing a second main lens surface optical power, the first and second main lens surfaces providing a main lens having a main lens optical power and a main optical axis defining radial, tangential and axial directions;

a first additional optical active part at the first side, the first additional optical active part providing a positive relative optical power with respect to the first main lens surface optical power, the first additional optical active part being positioned at a distance from the optical axis; and a second additional optical active part at the second side, the second additional optical active part fitting within a circumscribing circle around the main optical axis, and the second additional optical active part providing a relative optical power and/or an optical aberration with respect to (the optical power and/or an optical aberration of) the second main lens surface, wherein the distance between the main optical axis and the first additional optical active part is smaller than the diameter of the circle circumscribing the second additional optical active part such that the second optical active part at least partly overlaps with the first additional optical active part.

The second additional optical active part provides some additional optical power and/or optical aberration at the center of the IOL and is therefore available at narrow pupil sizes. The reading ability and depth of focus for distance vision at narrow pupil sizes is therefore increased, while distance vision itself not or hardly effected. Further, the second additional optical active part is easily provided at the second side, which in manufacturing of the IOL does not interfere with the complex geometry at the first side.

In an embodiment the second additional optical active part provides a positive relative optical power with respect to the second main lens surface optical power. The positive optical power does provide some additional effective optical power in the central range of the IOL, which assists in reading at narrower pupil sizes.

Such embodiment can be effectively achieved with the second additional optical active part providing a positive relative spherical optical power with respect to the second main lens surface optical power.

In another embodiment the second additional optical active part provides for an additional depth of focus. Having an increased depth of focus provides an improved near vision or reading ability.

Such embodiment is effectively achieved with an additional positive or negative spherical aberration with respect to an optical aberration of the second main lens surface. Having the (positive or negative) spherical aberration efficiently provides for an additional depth of focus around the optical power of the second main lens surface.

In an embodiment the second additional optical active part is arranged such that the main optical axis passes through the second additional optical active part.

In a preferred embodiment the second additional optical active part fits within a circumscribing circle having a diameter smaller than or equal to 3 millimeter, in an embodiment smaller than or equal to 2 millimeter, in an embodiment smaller than or equal to 1.5 millimeter. Having such dimensions provides an optimum between providing additional near vision power and not negatively influencing distance vision.

In an embodiment the second additional optical active part is substantially circular.

In an embodiment the second additional optical active part comprises a second additional optical power surface having a curvature stronger than a curvature of the second main lens surface, through which a positive additional optical power is easily provided.

In a further embodiment the second additional optical power surface is raised with respect to the second main lens surface, which will yield a rather smooth transition between the second main lens surface and the second additional power surface.

In an embodiment the first additional optical active part extends between the main optical axis and a circumference of the optic.

In a specific embodiment the distance between the main optical axis and the first additional optical active part is smaller than 2 millimeter, in an embodiment smaller than 1.5 millimeter, in an embodiment smaller than 1 millimeter, in an embodiment smaller than 0.5 millimeter.

In an embodiment the first additional optical active part in tangential directions is delimited by boundaries extending in substantially radial directions.

In an embodiment the optic comprises a central part at the first side, the central part being arranged such that the main optical axis passes through the central part, the central part having a relative optical power between −2 and 2 diopter with respect to the first main lens surface optical power. Having such central part at the first side provides for some further tuning capability of the effective optical power and/or depth of focus. It further provides for alignment tolerances of the IOL within the eye since it may prove difficult to exactly align the optical axis of the IOL with the optical axis of the eye.

In an embodiment the central part fits within a circumscribing circle, the circle having a diameter smaller than or equal to 3 millimeter, in an embodiment smaller than or equal to 2 millimeter, in an embodiment smaller than or equal to 1.5 millimeter, in an embodiment smaller than or equal to 1 millimeter, in an embodiment smaller than or equal to 0.5 millimeter. Such dimension provide an optimum trade-off to provide tolerances in centering the IOL in an eye, and the effects of the first and second additional power parts and the combined effect of both additional power parts.

In another embodiment the central part is substantially circular.

In a preferred embodiment the diameter of the circle circumscribing the central part is smaller than the diameter of the circle circumscribing the second additional optical active part.

In an embodiment the central part is adjacent to the first additional optical active part.

In another embodiment the optical power of the central part is substantially equal to the first main lens surface optical power, which provides a very well distance vision when distance vision should be the dominant capability of the IOL.

In an embodiment the first additional optical active part comprises a first additional optical power surface having a curvature stronger than a curvature of the first main lens surface.

In a further embodiment the first additional optical power surface is recessed with respect to the first main lens surface.

In an embodiment the positive relative optical power of the first additional optical active part with respect to the first main lens surface optical power is between 0.5 and 5 diopter, in an embodiment between 0.5 and 4 diopter, in an embodiment between 0.5 and 3 diopter.

In a preferred embodiment the positive relative optical power of the second additional optical active part with respect to the second main lens surface optical power is between 0.25 and 2 diopter, in an embodiment between 0.25 and 1 diopter. Such additional optical powers have some to work very well, while higher powers have shown to yield negative side effects on distance vision.

The first side may be an anterior side of the optic for facing away from a posterior chamber of the eye and the second side a posterior side of the optic for facing towards the posterior chamber, or the first side may be the posterior side and the second side the anterior side of the optic.

BRIEF DESCRIPTION OF THE DRAWINGS

Further features and advantages of the invention will become apparent by a description of the invention by way of non-limiting and non-exclusive embodiments. Embodiments of the invention will be described with reference to the accompanying drawings, in which like or same reference symbols denote like, same or corresponding parts, and in which.

DETAILED DESCRIPTION OF EMBODIMENTS

Figure 1:
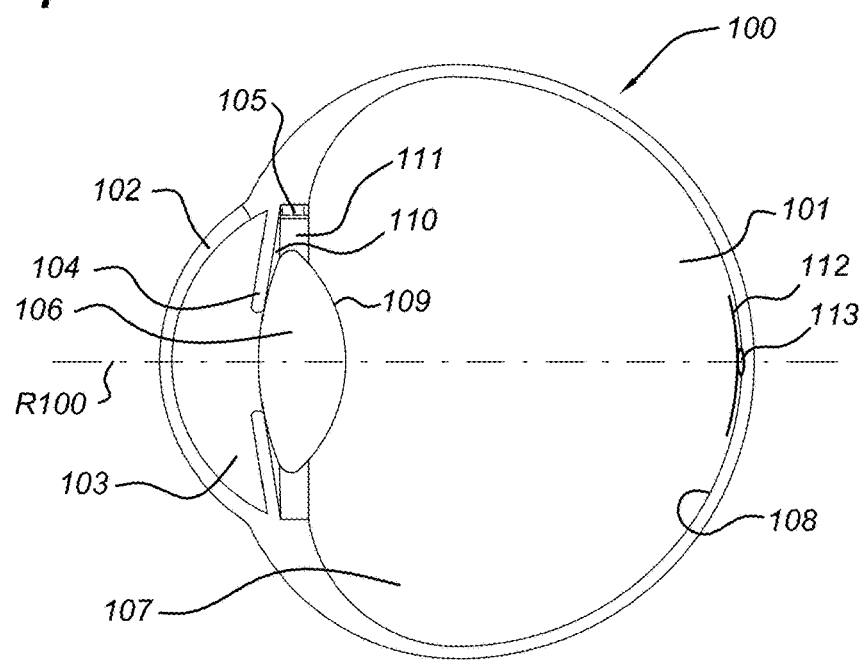
FIG. 1 shows a cross-section of the human eye.

A schematic view of a human eye 100 with its natural lens 106 inside lens capsule or capsular bag 109 is shown in FIG. 1. The eye has a vitreous body 101 within posterior chamber 107. Retina 108 is on the inside of the posterior chamber 107, which further comprises macula 112 with fovea 113 at the center thereof. The macula contains the photoreceptor cells, the fovea predominantly having cone photoreceptor cells although it does not have a sharply defined boundary. It merely shows a gradual transition from an area having a high density of (cone) photoreceptor cells to a peripheral area that predominantly has rod photoreceptor cells at decreasing density going from the center of the macula outwards. An optical axis R100 of eye 100 passes through the center of iris 104 and the center of macula 112 and fovea 113. The eye further has a cornea 102 and an anterior chamber 103. The lens 106 and capsular bag 109 are held by ciliary muscle 105 and zonule fibres or ciliary zonules 111. The (ciliary) sulcus 110 is in between iris 104 and ciliary zonules 111.

The natural lens can be replaced by an intraocular lens (IOL). In other applications the IOL can be positioned in the sulcus 110 between iris 104 and capsular bag 109, or in the anterior chamber 103 in addition to the natural lens or in addition to another IOL replacing the natural eye lens.

The present invention provides an intraocular lens 1 of which an embodiment is shown in FIGS. 2-8. Intraocular lens 1 comprises so-called haptics 9, 9' and an optic 3 having a circumference 2. The haptics are intended for fixation purposes of the intraocular lens within the human eye. Optic 3 has a first side 3.1 and a second side 3.2. In the embodiment shown the first side 3.1 is intended for facing towards the anterior chamber 103 of the eye and the second side 3.2 for facing towards the posterior chamber 107 of the eye, which makes the first side 3.1 an anterior side and second side 3.2 a posterior side of the optic.

Figure 2:
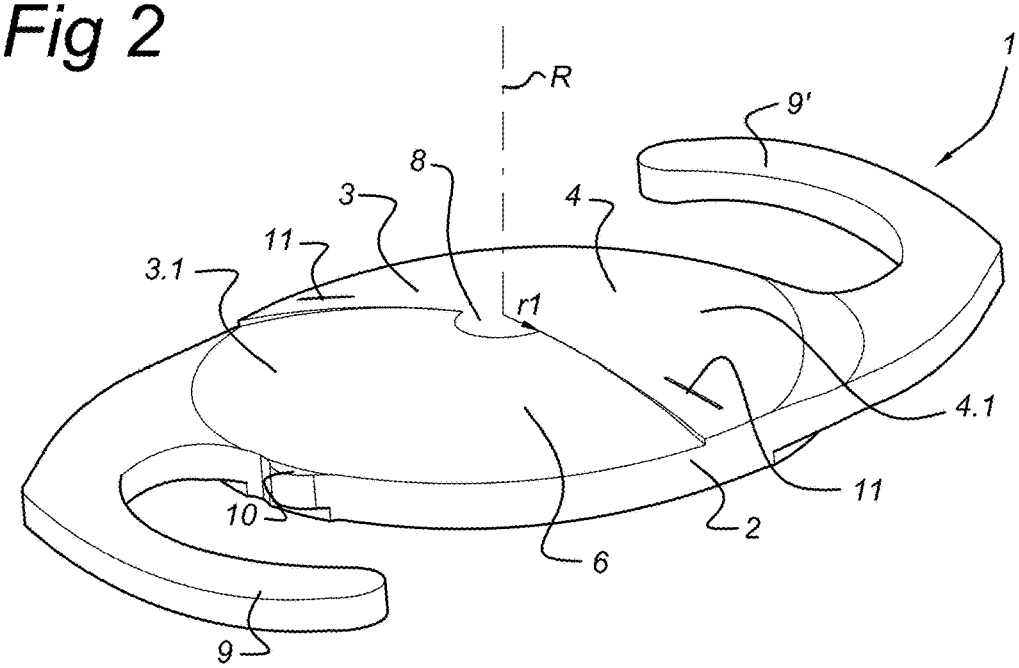
FIG. 2 shows a perspective view on a first (anterior) side of an embodiment of an intraocular lens according to the invention.
Figure 3:
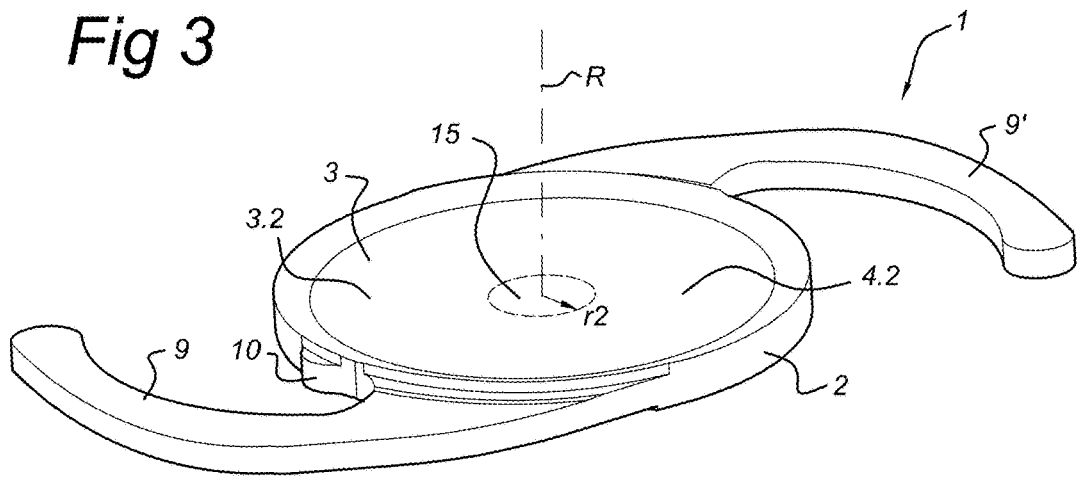
FIG. 3 shows a perspective view on a second (posterior) side of the embodiment of FIG. 2.
Figure 4:
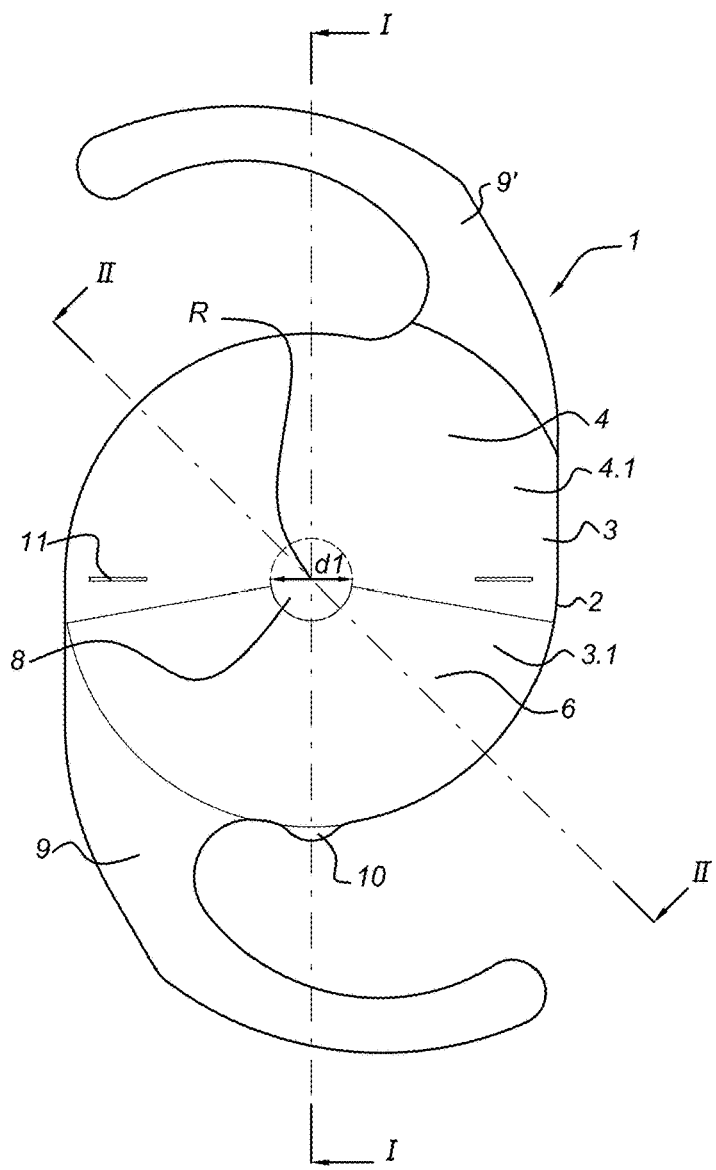
FIG. 4 shows a view on the first side of the FIG. 1 embodiment.
Figure 5:
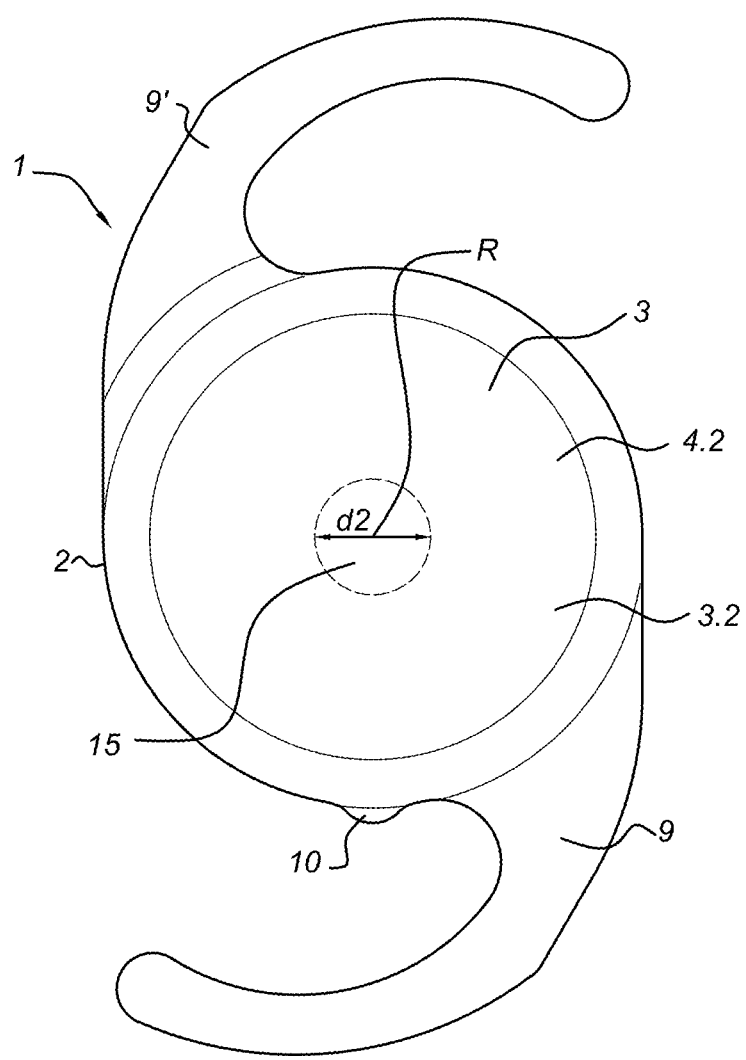
FIG. 5 shows a view on the second side of the FIG. 1 embodiment.
Figure 6:
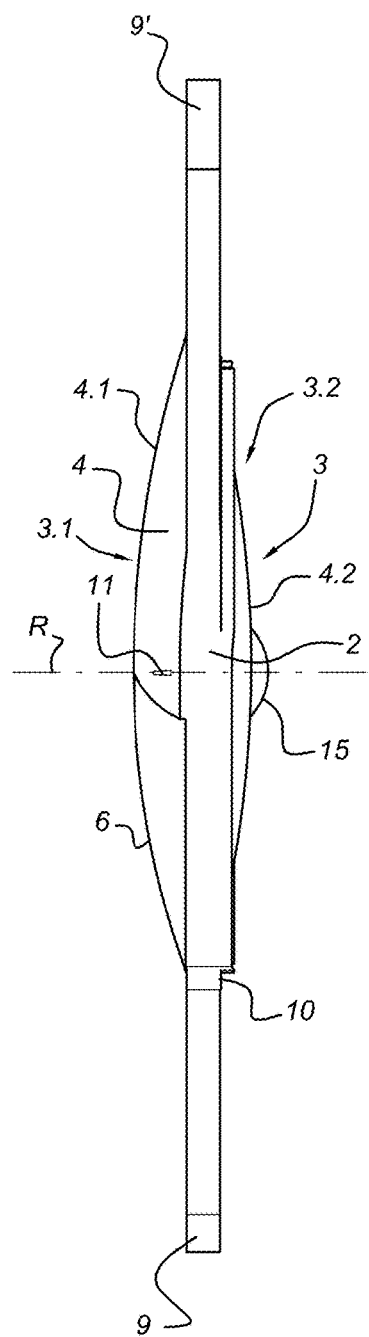
FIG. 6 shows a side view on the FIG. 1 embodiment.
Figure 7:
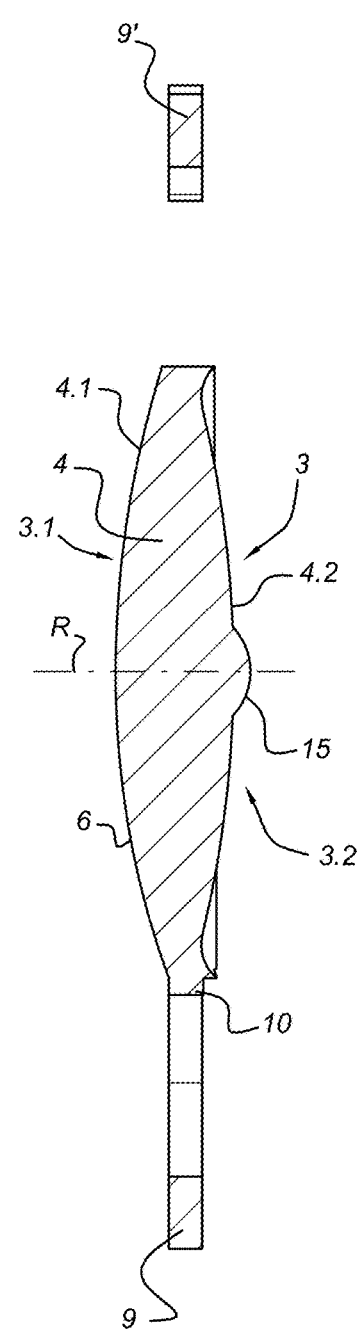
FIG. 7 shows a cross-section of the FIG. 1 embodiment along the line I-I in FIG. 4.
Figure 8:
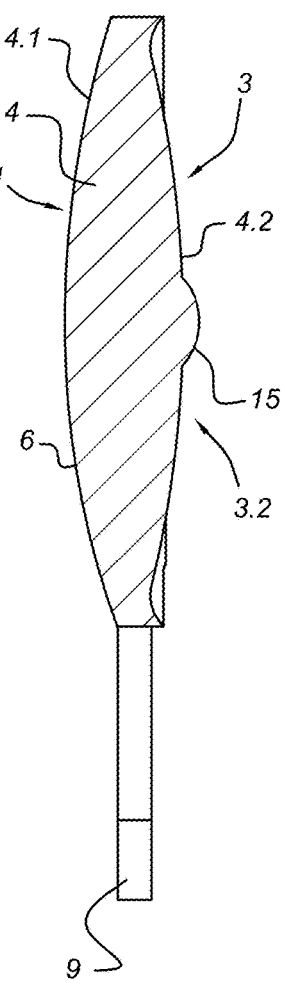
FIG. 8 shows a cross-section of the FIG. 1 embodiment along the line II-II in FIG. 4.

First side 3.1 of optic 3 comprises a first main lens surface 4.1 over approximately the top half of optic 3 as shown in FIGS. 2 and 4. Second side 3.2 comprises a second main lens surface 4.2 over substantially the full second side, except a central part 15, as is shown in FIGS. 3 and 5. First and second main lens surfaces 4.1, 4.2 together with the material of optic 3 make up a main lens 4. Main lens 4 has a main optical axis R going through the center of the optic. The main optical axis defines a radial direction perpendicular to the main optical axis, a tangential direction around the main optical axis, and an axial direction along the main optical axis. Alignment markers 10, 11 present on the intraocular lens can be used by the surgeon for correct positioning of the intraocular lens in the human eye during surgical implantation.

Main lens 4 of optic 3 of the intraocular lens is, in the embodiment shown, a main lens having its main optical axis R4 aligned with the optical axis R100 of the human eye when positioned in the human eye. Main lens 4 will generally be optimized for distance vision and an image will generally be projected around the center of the macula. Main lens 4 may provide optical correction for any imaging errors in the human eye. However, it may also be a (non-imaging) part having no optical power in case such optical correction is not required or not desired.

Optic 3 further comprises a first additional optical active part 6 at the first side 3.1. In the embodiment shown it extends between the main optical axis R and the circumference 2 of the optic, and is positioned at a distance from the optical axis R. The distance between the main optical axis and the first additional optical active part is smaller than 2 millimeter, in an embodiment smaller than 1.5 millimeter, in an embodiment smaller than 1 millimeter, and in another embodiment smaller than 0.5 millimeter. In tangential directions the first additional optical active part is delimited by boundaries extending in radial directions between the main optical axis R and the circumference 2 of the optic 3.

The first additional optical active part 6 provides a positive relative optical power with respect to the first main lens surface optical power between 0.5 and 5 diopter, in an embodiment between 0.5 and 4 diopter, in another embodiment between 0.5 and 3 diopter. The second main lens surface 4.2 at the second side 3.2 of the optic overlaps with the first additional optical active part 6 at the first side 3.1. Both surface together with the material of the optic 3 form a secondary lens having the positive relative optical power of the first additional optical active part 6 with respect to the main lens 4. Such positive relative optical power is intended to provide a good near or reading vision to the person having the IOL.

The positive relative optical power of the first additional optical active part 6 with respect to the first main lens surface 4.1 is achieved by a stronger curvature of the surface of the first additional optical active part 6 with respect to the curvature of the first main lens surface 4.1, which can be seen in FIG. 2. The surface of the first additional optical active part 6 is arranged such that it is recessed with respect to the first main lens surface 4.1.

FIGS. 2 and 4 further show that optic 3 has a central part 8 at the first side 3.1 of the optic. In the embodiment shown the central part is an extension of the first main lens surface 4.1. However, the central part may generally have a relative optical power between −1 and 2 diopter with respect to the main lens surface 4.1. The central part 8 is shown to be circular with a radius r1 and a diameter d1. Generally, the central part fits within a circumscribing circle around the optical axis and/or center of the optic. The diameter of the circumscribing circle has a diameter smaller than or equal to 3 millimeter, in an embodiment smaller than or equal to 2 millimeter, in an embodiment smaller than or equal to 1.5 millimeter, in an embodiment smaller than or equal to 1 millimeter, and in another embodiment smaller than or equal to 0.5 millimeter. In the embodiment shown the central part 8 is circular having a diameter of 0.6 millimeter.

The second side 3.2 of optic 3 is shown in FIGS. 3 and 5. The second side comprises over a substantial part the second main lens surface 4.2. At the center of the optic around the main optical axis R the second side comprises a second additional power part 15. The second additional power part 15 has a positive relative optical power with respect to the second main lens surface optical power. The relative optical power is between 0.25 and 2 diopter, in an embodiment between 0.25 and 1 diopter, and especially 0.75 diopter. The surface of the second additional optical active part 15 has a curvature that is stronger than a curvature of the second main lens surface 4.2, and is raised with respect to the second main lens surface. The stronger curvature and the surface of the second additional power part 15 being raised is shown in an exaggerated fashion in FIGS. 6 to 8. The second additional power part 15 is shown to protrude from second main lens surface 4.2.

The second additional power part 15 is shown to be circular with a radius r2 as shown in FIG. 3 and a diameter d2 (twice radius r2) as indicated in FIG. 5. Generally, the second additional optical active part has a shape fitting within a circumscribing circle having a diameter smaller than or equal to 3 millimeter, in an embodiment smaller than or equal to 2 millimeter, in an embodiment smaller than or equal to 1.5 millimeter. In the embodiment shown the second additional power part 15 is circular having a diameter of 1.5 millimeter.

The second additional power part 15 overlaps partly with the first additional power part 6 and partly overlaps with the first main lens surface 4.1. The second additional power part 15 therefore provides an additional power with respect to the main lens 4 and with respect to near vision lens provided by the first additional power part 6 in combination with the second main lens surface 4.2.

The intraocular lens can be made with known materials and by using known techniques such as moulding. Some parts, such as the first and second additional power parts 6, 15 may receive further turning steps to provide a specified optical power.

Various other embodiments of the invention will be apparent to the skilled person when having read the above disclosure in connection with the drawing, all of which are within the scope of the invention and accompanying claims.

The invention claimed is:

1. An intraocular lens (1) comprising an optic (3), the optic having first and second sides (3.1, 3.2) and comprising:
   a first main lens surface (4.1) at the first side (3.1) and a second main lens surface (4.2) at the second side (3.2), the first main lens surface providing a first main lens surface optical power and the second main lens surface providing a second main lens surface optical power,
   the first and second main lens surfaces providing a main lens (4) having a main lens optical power to provide distance vision, and a main optical axis (R) defining a radial direction perpendicular to the main optical axis, a tangential direction around the main optical axis and an axial direction along the main optical axis;

a first additional optical active part (6) at the first side (3.1), the first additional optical active part providing a positive relative optical power with respect to the first main lens surface optical power, the first additional optical active part (6) being positioned at a distance from the optical axis (R) and in tangential directions being delimited by boundaries extending in radial directions, and the first additional optical active part (6) overlapping with the second main lens surface (4.2) to form a secondary lens having the positive relative optical power of the first additional optical active part (6) with respect to the main lens (4) to provide near or reading vision;

a central part (8) at the first side (3.1), the central part being arranged such that the main optical axis (R) passes through the central part, and fitting within a circumscribing circle around the optical axis, the central part (8) being adjacent to the first additional optical active part (6), and the central part having a relative optical power between −2 and 2 diopter with respect to the first main lens surface optical power; and a second additional optical active part (15) at the second side (3.2), the second additional optical active part being arranged such that the main optical axis (R) passes through the second additional optical active part, and fitting within a circumscribing circle around the main optical axis (R), and the second additional optical active part providing a relative optical power and/or an optical aberration with respect to the second main lens surface, wherein the distance between the main optical axis (R) and the first additional optical active part (6) is smaller than the radius of the circle circumscribing the second additional optical active part (15), the diameter of the circle circumscribing the central part (8) being smaller than the diameter of the circle circumscribing the second additional optical active part (15), such that the second optical active part at least partly overlaps with the first additional optical active part (6) and partly overlaps with the first main lens surface (4.1).

2. The intraocular lens according to claim 1, wherein the second additional optical active part (15) provides a positive relative optical power with respect to the second main lens surface optical power.

3. The intraocular lens according to claim 2, wherein the second additional optical active part (15) provides a positive relative spherical optical power with respect to the second main lens surface optical power.

4. The intraocular lens according to claim 1, wherein the second additional optical active part (15) provides for an additional depth of focus.

5. The intraocular lens according to claim 4, wherein the second additional optical active part (15) provides for an additional positive or negative spherical aberration with respect to an optical aberration of the second main lens surface.

6. The intraocular lens according to claim 1, wherein the second additional optical active part (15) fits within a circumscribing circle having a diameter selected from the group consisting of smaller than or equal to 3 millimeter, smaller than or equal to 2 millimeter, and smaller than or equal to 1.5 millimeter.

7. The intraocular lens according to claim 1, wherein the second additional optical active part (15) is circular.

8. The intraocular lens according to claim 2, wherein the second additional optical active part (15) comprises a second additional optical power surface having a curvature stronger than a curvature of the second main lens surface (4.2).

9. The intraocular lens according to claim 8, wherein the second additional optical power surface is raised with respect to the second main lens surface (4.2).

10. The intraocular lens according to claim 1, wherein the distance between the main optical axis (R) and the first additional optical active part (6) is selected from the group consisting of smaller than 2 millimeter, smaller than 1.5 millimeter, smaller than 1 millimeter, and smaller than 0.5 millimeter.

11. The intraocular lens according to claim 1, wherein the central part (8) fits within a circumscribing circle, the circle having a diameter selected from the group consisting of smaller than or equal to 3 millimeter, smaller than or equal to 2 millimeter, smaller than or equal to 1.5 millimeter, smaller than or equal to 1 millimeter, and smaller than or equal to 0.5 millimeter.

12. The intraocular lens according to claim 1, wherein the central part (8) is circular.

13. The intraocular lens according to claim 1, wherein the first additional optical active part (6) comprises a first additional optical power surface having a curvature stronger than a curvature of the first main lens surface (4.1).

14. The intraocular lens according to claim 13, wherein the first additional optical power surface is recessed with respect to the first main lens surface (4.1).

15. The intraocular lens according to claim 1, wherein the positive relative optical power of the first additional optical active part (6) with respect to the first main lens surface optical power is selected from the group consisting of between 0.5 and 5 diopter, between 0.5 and 4 diopter, and between 0.5 and 3 diopter.

16. The intraocular lens according to claim 2, wherein the positive relative optical power of the second additional optical active part (15) with respect to the second main lens surface optical power is selected from the group consisting of between 0.25 and 2 diopter, and between 0.25 and 1 diopter.

* * * * *